United States Patent [19]

Berrens

[11] Patent Number: 5,770,698
[45] Date of Patent: Jun. 23, 1998

[54] PROCESS FOR THE PURIFICATION OF AQUEOUS EXTRACTS CONTAINING ALLERGENICALLY ACTIVE PROTEINS, EXTRACTS OBTAINABLE ACCORDING TO THIS PROCESS AS WELL AS THEIR USE

[75] Inventor: Lubertus Berrens, Utrecht, Netherlands

[73] Assignee: C.B.F. Leti S.A., Madrid, Spain

[21] Appl. No.: 403,832

[22] PCT Filed: Sep. 21, 1992

[86] PCT No.: PCT/NL92/00160

§ 371 Date: Aug. 14, 1995

§ 102(e) Date: Aug. 14, 1995

[87] PCT Pub. No.: WO94/06821

PCT Pub. Date: Mar. 31, 1994

[51] Int. Cl.$^6$ .............................. A61K 35/78; C07K 14/00
[52] U.S. Cl. ....................... 530/379; 530/370; 530/372; 530/412; 530/416; 530/417; 530/427
[58] Field of Search ..................................... 530/379, 370, 530/372, 412, 416, 417, 427

[56] References Cited

FOREIGN PATENT DOCUMENTS 0387952  9/1990  European Pat. Off. .

OTHER PUBLICATIONS

Guerin et al, *J. Immunol. Methods,* vol. 55, pp.265–271, 1982.
Marcy, *Chemical Abstracts,* vol. 83, p. 370, Ref. #81847f, 1975 (Fr. Patent No. 2,228,070, Nov. 29, 1974).

*Primary Examiner*—Cecilia J. Tsang
*Assistant Examiner*—Abdel A. Mohamed
*Attorney, Agent, or Firm*—Cushman Darby & Cushman IP Group of Pillsbury Madison & Sutro, LLP

[57] ABSTRACT

The invention concerns the removal of various allergologically irrelevant low-molecular weight components from the usual aqueous extracts of allergenically active proteins of plant pollens. Described are the desorption and subsequent elimination, from traditionally prepared allergenic pollen protein extracts, of low-molecular weight pigment and other compounds which are normally retained by strong electrostatic and/or hydrophobic forces. The preparation of such depigmented pollen proteins does not impair their allergenic potency or immunological specificity. The invention enables the production of fully active allergenic pollen proteins devoid of adhering low-molecular weight substances interfering with their safety, diagnostic accuracy and clinical efficacy. The purified pollen proteins represent improved starting materials for chemical derivatization, i.e. the preparation of attenuated vaccines for immunotherapy. The invention also provides suitable products for investigating the molecular structure of allergenic epitopes.

9 Claims, 2 Drawing Sheets

PROCESS FOR THE PURIFICATION OF AQUEOUS EXTRACTS CONTAINING ALLERGENICALLY ACTIVE PROTEINS, EXTRACTS OBTAINABLE ACCORDING TO THIS PROCESS AS WELL AS THEIR USE

BACKGROUND OF THE INVENTION

1. Field of the Invention

The present process relates to a process for the purification of aqueous extracts containing allergenically active proteins and further containing non-allergenic undesirable compounds.

Aqueous extracts of the pollen grains of grasses, weeds, trees and other plants have since the turn of this century found widespread application for the in vivo and in vitro diagnosis of hayfever ("pollinosis") in predisposed human, so-called "atopic" patients. Since the first description by Noon and Freeman in 1911, such extracts have also been used for the treatment of this ailment by applying them in a regimen of injections for long-term "desensitization", "hyposensitization", or "immunotherapy". Based on the observation that the causative major allergenic components in extracts of pollen are proteins in the molecular weight range of 20–70 kD, whereas the constituents below the 10 kD molecular weight range are believed to be non-allergenic, it has become common practice in the manufacturing process of pollen extracts for diagnosis and immunotherapy to dialyse or ultrafilter the aqueous pollen extracts through membranes of 5–10 kD nominal cut-off in order to remove supposedly irrelevant components with a molecular size lower than 5–10 kD, thereby retaining the allergenic proteins in the molecular size range of 10–100 kD in order to improve the quality of the allergenic extract for clinical application.

2. Description of Related Art

A number of reports has nevertheless in the past appeared in the scientific literature relating to the possible allergenic properties of the low-molecular weight and dialysable constituents of aqueous pollen extracts, i.e. substances with an upper limit molecular weight of about 10 kD ( Moore M B and Moore E E. J Am Chem Soc 1931; 53: 2744; Unger L, Cromwell H W, Moore M B. J Allergy 1932; 3: 253).

These investigations indicated that the low-molecular constituents of M<5 kD from pollen extracts do indeed exhibit some residual allergenic activity, although their potency on a weight basis is a factor of at least 1000 less than that of the non-dialysable glycoproteins of M>5 kD. These results, together with the highly complex chemical composition of the dialysable fraction of pollen extracts provided little impetus for pursuing these studies. The state of the prior art therefore is that the low-molecular weight components of M<5 kD in pollen extracts are irrelevant in terms of their allergological and immunological contribution.

However, the content and biological activity of the water-soluble flavonoid-glycosides present in nearly every pollen extract has nevertheless remained ambiguous. It is usually tacitly assumed that such compounds, which may considerably influence cellular functions in man and animals after parenteral administration, are being removed during the dialysis process (Wiermann R, Wollenweber E, Rehse C, Z Naturforsch 1981; 36 c: 204). Nevertheless, spectroscopic examination of the dialysed conventional pollen extracts containing proteins of M>10 kD for diagnosis and therapy shows that a very high proportion of (flavonoid-) pigments remains firmly adsorbed to the proteins (compare FIG. 1).

SUMMARY OF THE INVENTION

The present invention provides a process for the purification of aqueous extracts containing allergenically active proteins and further containing non-allergenic undesirable compounds, which process yields highly purified extracts containing substantially allergenically active proteins, which extracts do not suffer from the (not always recognized) disadvantages of the conventional aqueous extracts containing allergenically active proteins.

BRIEF DESCRIPTION OF THE DRAWINGS

FIG. 2 projects the successful removal of the adsorbed flavonoid pigments as recorded by a UV-absorption spectra.

DETAILED DESCRIPTION OF PREFERRED EMBODIMENTS

Figure 1:
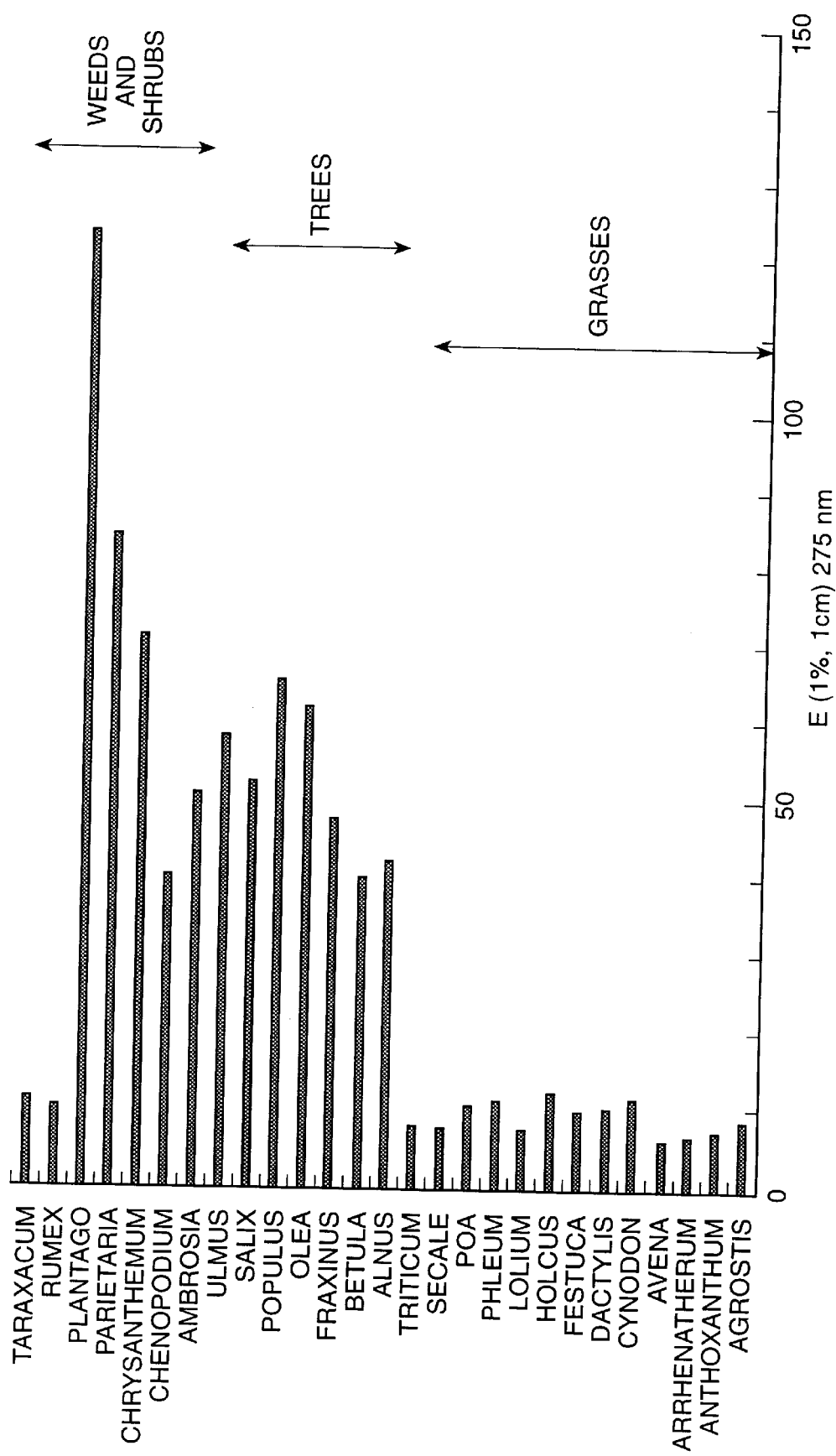
FIG. 1 depicts the extinction values at 260–280 nm of aqueous solutions of classical pollen proteins HMW, pre-dialysed at neutral pH but before acid desorption and re-dialysis.

In a first embodiment the present invention relates to a process for the purification of aqueous extracts containing allergenically active proteins and further containing non-allergenic undesirable compounds, wherein said non-allergenic compounds adhering to said proteins are removed from said proteins by using means which disrupt electrostatic forces and/or hydrophobic forces being responsible for the adherence of said non-allergenic compounds to said proteins.

Specifically, the process according to the invention comprises the following steps:

1) providing an aqueous extract containing allergenically active protein(s) and further containing non-allergenic undesirable compounds as a starting material,
2) subjecting said starting material to a treatment to remove said non-allergenic compounds, which adhere to said proteins, from said proteins in which means are used which disrupt electrostatic forces and/or hydrophobic forces being responsible for the adherence of said non-allergenic compounds to said proteins, to obtain an aqueous extract substantially free from said adhering undesirable compounds,
3) collecting the substantially pure extract.

Further embodiments of the present invention will be apparent from herebelow.

According to the invention it was established that impurities such as flavonoids and/or glycosides, but also other compounds, exemplified in the below, are contained in the usual extracts, but not in a "free" form. The "adherence" of the impurities to the allergenically active proteins may be based on Van der Waals forces, ionic bonding, hydrophobic interaction or even chemical interaction (covalent forces).

The expression "means which disrupt electrostatic forces, hydrophobic or other physical forces" relates to various chemical and/or physical means which are effective for the removal of adsorbed or (firmly) adhered compounds (impurities) from the allergenically active proteins.

In a preferred embodiment of the process of the invention the means for disrupting electrostatic or other physical forces are selected from the group of chemical means consisting of acid, and alkaline materials including anion- and cation-exchanging materials, salts and electric currents.

It will be apparent that the removal of adsorbed impurities may not only be performed by changing the electrical environment (electrical charges) in the extract used as starting material, but also by the use of forces which influence the dielectric constants of the proteins in question. Means which influence hydrophobic interactions and Van der Waals forces may equally be used.

In the process of the invention it is preferred to use chemical means, in particular acid, in an amount causing the exceeding of the iso-electric point of the allergenically active proteins aimed at. It is preferred to use an acid having a pH-value of less than 3, preferably a pH-value in the range of 1.5–2.5. It will be clear that these pH-values are in general below the iso-electric points of almost every protein.

In the case of the use of an alkali a pH-value of e.g. 9–11, i.e. above the usual electric points, may be used.

This means that the acid and alkali concentrations may be in the order of 0.1 N to 0.01 N for (strong) acids and 0.01–0.001 N for (strong) alkali.

If, on the other hand, it is desirable to dissociate or desorb low-molecular compounds with salts at neutral pH in the range of e.g. pH 6–8, the absolute salt concentration or ionic strength is relevant. Preferably, monovalent salts are used, e.g. NaCl, KCl, KCNS, the corresponding bromides, or e.g. guanidine-HCl. It is preferred that the value of the ionic strengths is between 2–6 M, preferably 2–5 M. It should be noted that higher concentrations, e.g. of guanidine-HCl, tend to disrupt hydrogen bonds of the carrier protein as well as inter-chain linkages of composite proteins. However, on the other hand such a disruption may not be disadvantageous as in many cases the allergenity or antigenicity may be retained. It is supposed that these immunological properties are maintained by virtue of epitopes on the secondary structure of the proteins, which are responsible for this specific activity.

In a further embodiment of the present invention the means for disrupting electrostatic forces and physical forces comprise electric currents in the form of electrophoresis. Normally, the electrophoresis is carried out with the aqueous extracts. Normally, electrophoresis should not be performed too long in order to avoid local heat exposure or (complete) denaturation of the protein. Furthermore, a reasonably high electrical potential across the applied electrodes should be used, e.g. in general between 10–2000 Volts DC, in particular between 200–1000 Volts DC. If the potential is too high, the protein carriers themselves may suffer some pertubation of their colloid-chemical zeta potential, thereby irreversibly causing unfolding of the tertiary or even secondary structure and a loss of the stabilizing water layer. Of course, the electrical current is dependent on the salt concentration in the solution, normally a buffer solution.

Although according to the process of the invention normally non-allergenic compounds having a molecular weight of less than 10,000, preferably less than 5000 are removed, it will be apparent that with equal good results also compounds having a lower molecular weight, e.g. less than 1000, may be removed from the proteins.

However, preferably flavonoids and/or glycosides are removed.

Flavonoids—occurring in the present aqueous extracts—affect arachidonic acid metabolism and interact as phenols or quinoid derivatives with macromolecules, causing for example enzyme inactivation due to complex formation with tannin-like polymers. Strong interaction with proteins is in fact a general property of polyphenols (among them the flavonoids), their oxidation products and their polymers. As mentioned in the above the interaction of the impurities being present in the extracts used as starting materials in the process of the invention can be physical (Van der Waals forces, ionic bonding, hydrophobic interactions) or chemical (covalent forces by interaction with oxidized (bi-)phenols. Flavonoids and flavonoidglycosides as individual molecules inhibit histamine release from mast cells and basophils and modulate to a considerable degree the normal functions of polymorphonuclear leucocytes and neutrophils. These biological activities may have considerable impact on the outcome of diagnostic skin and inhalation tests with prior art preparations routinely performed in allergic patients. On the other hand, it has already been extensively documented in European Patent Application No. 90200562.8 that low-molecular weight (M<5000) water-soluble and non-adsorbed flavonoid-glycosides do not contribute to the binding of IgE antibodies in the serum of specifically sensitized allergic patients. The removal of impurities such as flavonoids and their glycosides from the customary diagnostic and therapeutic pollen protein vaccines may therefore improve their usefulness and efficacy in clinical medicine.

A further argument for eliminating adsorbed low-molecular compounds from plant pollen proteins administered to man is that many pollen species, like the plants elaborating them, may contain low-mass (M<1000) non-flavonoid organic compounds potentially harmful to man, e.g. toxic alkaloids, benzochinones, terpenoids and their derivatives irritating to mucous membranes, and other aromatic structures. Like the flavonoids, such components may in some instances resist simple dialysis or ultrafiltration at neutral pH through membranes of 10 kD nominal cut-off by remaining firmly adsorbed to proteins by physical forces.

The invention also relates to extracts obtainable according to the processes of the invention as described herein. Such purified extracts ensure the safety of allergenic plant pollen extracts intended for the diagnosis and treatment of allergic diseases.

According to the present invention a broad variety of extracts of naturally occurring materials may be (further) purified. Representative examples are:

Pollen Extracts

The following tree pollens, grass pollens and weed pollens:

Tree pollens:

*Acacia Longifolia, Acacia baileyana, Ailanthus altissima, Alnus tenuifolia/icnana, Alnus rubra, Alnus sinuata, Prunus amygdalus, Pyrus malus (Malus pumila), Prunus armeniaca, Thuja orientalis, Fraxinus velutina, Fraxinus nigra, Fraxinus pennsylvanica, Fraxinus oregona, Polulus tremuloides, Myrica gale, Fagus grandifolia, Betula lenta, Betula papyrifera, Betula fontinalis, Betula alba, Betula verrucosa, Betula lutea, Carpinus carolineana, Callistemon citrinus, Juglans cinerea, Ceratonia siliqua, Cedrus deodora, Thuja plicata, Linocedrus decurrens, Cryptomeria japonica, Chamaecyparis lawsoniana, Juniperus virginiana, Juniperus scopulorum, Tamarix gallica, Thuja occidentalis, Prunus cerasus, Castanea dentata, Aesculus hippocastanum, Populus trichocarpa, Populus deltoides, Populus fremontii, Cupressus arizonica, Taxodium distichum, Cupressus sempervirens, Cupressus macrocarpa, Sambucus glauca, Ulmus crassifolia, Ulmus parvifolia, Ulmus pumila, Ulmus fulva, Eucalyptus globulus, Pseudotsuga menziesii, Abies nobilis (procera), Abies concolor, Liquidambar styraciflua, Celtis occidentalis, Corylus americana, Tsuga canadensis, Tsuga heterophylla, Carya ovata, Carya laciniosa, Carya tomentosa, Ostrya virginiana, Juniperus californica, Juniperus chinensis, Juniperus monosperma, Juniperus pinchotti, Juiniperus osteosperma (Juniperus utahensis), Juniperus occidentalis,*

*Syringa vulgaris, Tila americana, Robina pseudoacacia, Acer macrophyllum, Acer saccharum, Acer rubrum, Acer saccharinum, Acer negundo, Melaleuca leucadendron, Prospopis juliflora, Philadelphus lewisii, Broussonetia papyifera, Morus rubra, Morus alba, Quercus gambelii, Quercus chrysolepsis, Quercus velutina, Quercus marilandica, Quercus macrocarpa, Quercus kelloggii-californica, Quercus dumosa, Quercus agrifolia, Quercus engelmanii, Quercus garryana, Quercus ilex, Quercus wislenzenii, Quercus stellata, Quercus rubra, Quercus palustris, Quercus lobata, Quercus virginiana, Quercus nigra, Olea europaea, Citrus sinensis, Maclura pimifera, Phoenix dactylifera, Chamaerops humulis, Phoenix canariensis, Cocos plumosa, Prunus persica, Pyrus communis, Carya pecan, Schinus molle, Schinus terebinthifolius, Casuarina equisetifolia, Pinus nigra, Pinus canariensis, Pinus sabiniana, Pinus taeda, Pinus contorta, Pinus radiata, Pinus edulis, Pinus resinosa, Pinus echinata, Pinus virginiana, Pinus pondersa, Pinus strobus, Pinus monticola, Prunus domestica, Populus balsamifera, Populus nigra-italica, Polulus trichocarpa, Populus alba, Sequoia sempervirens, Elaeagnus angusti-folia, Picea rubens, Picea sitchensis, Platanus occidentalis, Platanus acerifolia, Platanus racemosa, Larix occidentalis, Tamarix gallica, Ailanthus altissima, Juglans rupestris, Juglans nigra, Juglans hindsii, Juglans californica, Juglans regia, Salix lasiolepis, Salix nigra, Salix discolor, Salix laevigata, Salix lasiandra, Juniperus sabinoides, Plantago lanceolata, Fraxinus americana, Quercus alba, Aces negundo, Alnus rhombifolia, Ulmus americana;*

Grass and Weed Pollens:

*Hordeum vulgare, Agrostis tenuis, Poa annua, Poa compressa, Poa pratensis, Poa sandbergii, Bromus rigidus, Bromus carinatus, Bromus secalinus, Bromus inermis, Bromus mollis, Agropyron spicatum, Phalaris canariensis, Phalaris arundinacea, Festuca rubra, Bouteloua gracilis, Koeleria cristata, Eragrostis variabilis, Avena sativa, Avena elatior (Arrhenatherum elatius), Agropyron repens, Agrostis alba, Secale cereale, Elymus triticoides, Elymus cinereus, Lolium multiflorum, Elymus glaucus, Distichlis stricta, Sorghum vulgare, Sorghum vulgare var. sudanese, Anthoxanthum odoratum, Holcus Ianatus, Triticum aestivum, Agropyron smithii, Medicago sativa, Aseter sinensis, Balsamorhiza sagittata, Bassia hyssopifolia, Franseria bipinnatifida, Hymenoclea salsola, Amaranthus palmeri, ricinus communis, Typha latifolia, Trifolium pratense, Melilotus officinalis, Trifolium repens (album), Xanthium strumarium, Xanthium spinosum, Cosmos bipinnatus, Narcissus pseudonarcissus, Dahlia pinnata x coccinea, Chrysanthemum leucanthemum, Taraxacum officinale, Rumex obtusifolius, Rumex cripus, Anthemix cotula, Epilobiium angustifolium, Gladiolus Xhortulanus, Sarcobatus vermiculatus, Cannabis sativa, Humulus lupulus, Grayia spinsa, Allenrolfea occidentalis, Kochia scoparia, Lilium longiflorum, Tagetes patula, Iva xanthifolia, Iva angustifolia, Iva ciliata, Chenopodium ambrosiodes, Brassica nigra, Brassica campestris, Urtica dioica, Salicornia ambigua, Amaranthus retroflexus, Amaranthus spinosus, Eschoscholzia californica, Iva axillaris, Chrysothamnus nauseosus, Franseria deltoides, Franseria ambrosiodes, Franseria dumosa, Franseria acanthicarpa, Ambrosia trifida, Ambrosia artemisiifolia (elatior), Dicoria canescens, Franseria tenuifolia, Ambrosia bidentata, Rosa multiflora, Arthemisia californica, Artemisia dracunculus, Artemisia vulgaris heterophylla, Artemisi frigida, Artemisia pycnocephala, Artemisia ludovician, Atriplex wrightii, Atriplex polycarpa, Atriplex serenana bracteosa, Atriplex lentiformis breweri, Atriplex lentiformis, Atriplex rosea, Atriplex argentea expansa, Atriplex patula hastata, Atriplex canescen, Cytisus scoparius, Suaeda californica, Carex barbara, Atriplex confertifolia, Rumex acetosella, Antirrhinum majus, Beta vulgaris, Helianthus annuus, Acnida tamariscina, Eurotia lanata, Chenopodium botrys, Artemisia absinthium, Parietaria judaica, Parietaria officinalis.*

Epidermals and Glandular Elements:

Camel Hair & Dander; Cattle Hair & Dander; Cat Hair and Dander; Deer Hair & Dander; Feathers, Chicken; Feathers, Duck; Feathers, Goose; Feathers, Parakeet; Feathers, Pigeon; Feathers, Turkey; Fox Fur; Gerbil Hair & Epithelium; Goat Hair & Dander; Guina Pig Hair & Dander; Hamster Hair & Epithelium; Hog Hair & Dander; Horse Hair & Dander; Human Dander; Monkey Hair & Epithelium; Mouse Hair & Epithelium; Dog Breeds Hair & Dander; Pyrethrum; Rabbit Hair & Epithelium; Rat Hair & Epithelium;

Dust and Miscellaneous Extracts:

Coconut Fiber; Cotton Linters; Cottonseed; Dust, Barley; Dust, Corn; Dust, House; Dust, Grain Mill; Dust, Mattress; Dust, Oat; Dust, Pea; Dust, Rye; Dust, Soybean; Dust, Upholstery; Dust, Wheat; Dust, Wood-Cedar/Juniper; Dust, Wood-Fir/Hemlock; Dust, Wood-Gum; Dust, Wood-Mahogony; Dust, Wood-Maple; Dust, Wood-Oak Mix; Dust, Wood-Pine Mix; Dust, Wood-Redwood; Dust, Wood-Spruce; Dust, Wood-Walnut; Fern Spores sp.; Flax Fiber, Flaxseed; Hemp; Jute; Kapok; Karaya Gum; Lycopodium; Orris Root, Pyrethrum; Silk; Sisal; Tobacco; Soybean; Castor bean;

Insect Extracts:

Ant, (Black and Red); Ants, Carpenter; Ants, Fire; Blakfly; Butterfly; Caddis Fly; Cricket; Cockroach; Deer Fly; Flea antigen; Fruit Flies; Gnat sp.; House Fly; Mayfly Sp.; Mite (*D. farinae, D. pteronyssimus, Lepidaglyphus* spp.); Moth.

The present invention also relates to the use of the purified extracts obtainable according to the invention, for standardization, diagnosis, synthesis, and vaccination purposes.

Specific embodiments of the present invention are illustrated by the following procedures A–C.

Procedure A

Pollen granules are collected from botanically identified plants and dried in air at ambient temperature. Lipids, fatty acids, free flavonoids and other apolar free organic substances are then removed from the dry pollen by continuous extraction in a Soxhlet apparatus with organic solvents non-miscible with water, e.g. dry diethylether or n-hexane. The defatted pollen mass is again dried in air and subsequently extracted for 2 hours under mechanical agitation at a temperature between 4–20° C. with aqueous solvents, i.e. dilute buffer or ammonium bicarbonate solutions, or with distilled water at a pH-value maintained between 6–8.5. The mixture is then centrifuged for 30 minutes at about 3000–5000 r.p.m., and the supernatant fluid is collected. The insoluble residue is discarded or may be re-extracted once more by the same procedure. The (combined) aqueous extract(s) is clarified by filtration through ordinary filter paper and then dialysed for 18 h against several changes of distilled water with a pH-value no lower than 5.5–6.0 and no higher than pH 7.5. For the dialysis step use is made of commercial membranes with a nominal cut-off of 5–10 kD (e.g. Visking cellophane dialysis tubing) or, alternatively, the extract may be diafiltered through suitable membranes of the same cut-off range (e.g. Amicon or Millipore Ultra- or DiaFilter Membranes). The non-dialysable retentate solution, containing the high molecular (HMW) allergenic proteins is finally taken to dryness by lyophilisation, or processed directly from solution for further purification of the allergenic proteins of M>5–10 kD.

In the present procedure the lyophilised material HMW is redissolved in distilled water to a concentration of 0.5–1.0% w/v and the pH of the solution is adjusted to pH 2 by the dropwise addition of 6N( or more concentrated) HCl. The extract is then redialysed for 24 h at a temperature between 4–20° C. against 100 volumes of distilled water (pH 6–7.5) as the outer liquid. During this process the outer liquid is kept under constant agitation by placing the vessel holding both the outer liquid and the free-floating dialysis bags on a magnetic stirrer. After terminating the trans-membrane passage of the desorbed pigments, the pH-value of the outer fluid has risen to about pH 3.5. It was found that the use of acidified water at pH 2 as the outer liquid directly at the start of the process does not improve the efficiency of the release of adsorbed pigments. After the separation process, the retentate fluid inside the dialysis bag or retained by the diafilter membrane is brought to pH 6.5–7.5 under stirring by the dropwise addition of 1N NaOH. The thus neutralized solution is finally dried by lyophilisation to recover the depigmented allergenic pollen proteins DPP as end product. As discussed in Example III, it was shown in the present procedure that the lowering of the pH by itself does not seriously impede the antibody recognition sites of the allergenic proteins.

Depending on the nature and species of the pollen grains, the procedure outlined above removes 15–65% w/w of adsorbed pigments relative the dry weight of the orginal allergenic pollen protein preparation HMW (table I). The desorbed pigment material, which in some cases also contains small peptides, may be recovered separately by concentrating the neutralised outer liquid under reduced pressure in a rotating thin-film evaporating apparatus.

TABLE I

Recoveries of depigmented pollen proteins of M > 10 kD from proteins predialysed at M > 10 kD nominal cut-off after removal of adsorbed pigments and compounds of less than M = 10 kD, together with the percentages of desorbed molecules of M < 10 kD.

| Pollen | % yield depigmented proteins M > 10 kD | % yield desorbed compounds M < 10 kD |
|---|---|---|
| *Lolium perenne* | 67 | n.d. |
| *Dactylis glomerata* | 68 | 17 |
| *Artemisia vulgaris* | 63 | 18 |
| *Betula alba* | 31 | 64 |
| *Chenopodium album* | 57 | 36 |
| *Olea europea* | 31 | 52 |
| *Ambrosia elatior* | 67 | n.d. |
| *Parietaria judaica* | 67 | 15 |

The process is controlled by ultraviolet absorption spectroscopy. As shown in FIG. 1, the extinction values at 260–280 nm of aqueous solutions of classical pollen proteins HMW, pre-dialysed at neutral pH but before acid desorption and re-dialysis, may achieve very high values, especially with the non-depigmented allergenic proteins of the pollens of the trees, weeds and shrubs. Estimates of the protein content from the extinction coefficients at 260–280 nm in many cases therefore leads to overestimates. The removal of adsorbed pigments causes a significant drop in the extinction coefficients in the 260–280 nm range as well as at 340–360 nm, the major absorption range of the flavonols (Table II).

TABLE II

Changes in UV-extinction coefficients E (1%, 1 cm) at pH2 (HCl) before and after depigmentation by acid dialysis.

| | Pollen preparation | | | |
|---|---|---|---|---|
| | 260 nm | | 350 nm | |
| | before | after % | before | after % |
| *Lolium perenne* | 7.6 | 9.5 + 26 | | |
| *Dactylis glomerata* | 10.0 | 5.9 − 41 | | |
| *Artemisia vulgaris* | 26.4 | 22.8 − 14 | | |
| *Betula alba* | 32.4 | 19.4 − 40 | 20.4 | 6.5 − 68 |
| *Chenopodium album* | 42.4 | 35.1 − 17 | 26.8 | 21.0 − 22 |
| *Olea europea* | 66.0 | 50.3 − 23 | 42.0 | 27.1 − 35 |
| *Ambrosia elatior* | 82.4 | 34.8 − 58 | 64.4 | 22.1 − 66 |
| *Parietaria judaica* | 108.3 | 103.8 − 4 | 64.8 | 70.4 + 8 |

The allergenic potency of the final depigmented product DPP is compared with that of the original pollen proteins HMW by inhibition of the binding of specific IgE- or IgG-class antibodies in the blood serum of specifically allergic pollinosis patients. The IgE-binding potency of the DPP product relative to the HMW preparation may for example be quantitatively determined by the chemical coupling of either the HMW or the DPP product to cellulose discs with cyanogen bromide or other coupling agents, followed by IgE antibody assay according to the established procedures of radioallergosorbent- or enzyme-allergosorbent tests. For quantitatively evaluating the reaction with specific human IgG-antibodies, either the DPP or the HMW proteins may be adsorbed physically to the surface of the wells of polystyrene microtiter plates, followed by established procedures of enzyme immunoassay.

Procedure B

In a modification of the production process, the allergenic proteins HMW are prepared from pollen granules as described in Procedure A, but the retentate solution at pH 5.5–7.5 containing the allergenic proteins of M>10 kD is not dried by lyophilization. Instead, the protein solution is directly brought to pH 2 by the dropwise addition of 6N HCL and the thus acidified solution is submitted to re-dialysis for 6–24 hours or to renewed ultrafiltration through membranes of M=10 kD nominal cut-off. The nondialysable retentate solution is then recovered, adjusted with 1N NaOH to pH 6.5–7.5 and dried by lyophilization.

Procedure C

The experience gained in the development of Procedures A and B of the invention demonstrates that the firm adsorption of flavonoid- or flavonoid-glycoside pigments to pollen proteins is largely due to electrostatic forces, which can be overcome for purposes of desorption by discharging negative carboxyl- and/or phenolic hydroxyl groups of either partner at a pH-value below 3.0. However, in case such conditions are considered undesirable for considerations of possible denaturation or loss of essential structural protein determinants, a procedure was developed based on the elimination of adsorbed pigments in an electric field in the neutral pH-range of 6.5–7.5.

In this method, a 2–5% solution is made of the lyophilised allergenic proteins HMW described in Procedure A, in a 0.01M inorganic buffer salt solution pH 6.5–7.5, for example a phosphate-buffered saline solution. A suitable volume of this solution, depending on the technical equipment chosen, is then subjected to free electrophoresis to disrupt the ionic forces causing protein-pigment adsorption. During the electrophoresis the pigments rapidly move to the cathode compartment and may thus be separated from the slow-moving protein constituents, which remain on the anodic side. A technical prototype of this Procedure is given in Example IV.

EXAMPLE I

Figure 2:
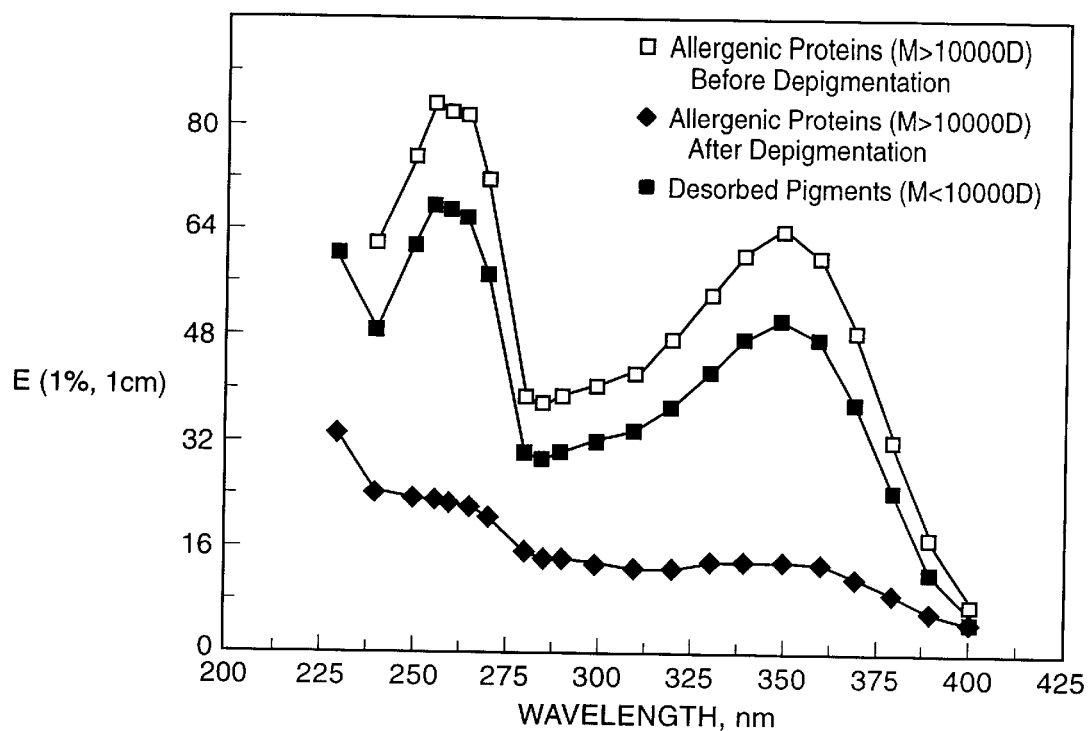
FIG. 2 depicts the results of Example I, where the process claimed in the invention was applied to *Ambrosia elatior*.

In this experiment the dry pollen of short ragweed pollen, *Ambrosia elatior* (obtained commercially from Beecham Research Laboratories, England) were defatted with diethylether and extracted with distilled water as described in Procedure A. Of the dialysed and lyophilized HMW ragweed pollen protein preparation, a sample of 25 mg was dissolved in 5 ml distilled water and the solution was brought to pH 2 by the dropwise addition of 6N HCl. The ultraviolet absorption spectrum was separately observed at 1:20 dilution in 0.01N HCl. The sample was dialysed under stirring and at ambient temperature for 24 hours against a total volume of 500 ml of distilled water. After the acid dialysis step, the UV-absorption spectrum of the inner retentate fluid was again observed at 1:2- dilution in 0.01N HCl. The outer liquid was concentrated to the original volume of 5 ml in a RotaVapor® thin-film evaporator and the UV-absorption spectrum measured in 1:20 dilution at pH 2. The successful removal of the adsorbed flavonoid pigments in this experiment is clearly demonstrated in the UV-absorption spectra recorded in FIG. 2 and the numerical extinction coefficients in Table II. The yield of lyophilized depigmented protein material DPP recovered according to Procedure A is listed in Table I.

EXAMPLE II

In these experiments, the same procedure as described in Example I was followed with the pollen of *Lolium perenne* and *Dactylis glomerata* as representative examples of potent allergenic pollens of the botanical family of the Gramineae, and of *Chenopodium album* and *Artemisia vulgaris* as well-known representatives of allergenic pollens of weeds. The numerical data with respect to yields of DPP from HMW as well as the pertinent spectroscopic figures are listed in Tables I and II. The results of these experiments show that the desorption of flavonoid (-glycoside) pigments from traditionally prepared allergenic pollen proteins HMW not only applies to pollen of the weed *Ambrosia elatior* as reported in Example I, but extends to other weeds as well as to the pollen of the grasses.

EXAMPLE III

In these experiments, the same procedure A as described in Examples I and II was followed with the potent allergenic pollens of the trees *Betula alba*, *Olea europea* and of the widespread Mediterranean weed *Parietaria judaica*. The original allergenic proteins HMW and the corresponding depigmented proteins DPP were examined for in vitro allergenicity by means of the inhibition of binding of specific IgE- and IgG-antibodies in the blood serum of specifically allergic patients.

Figure 3:
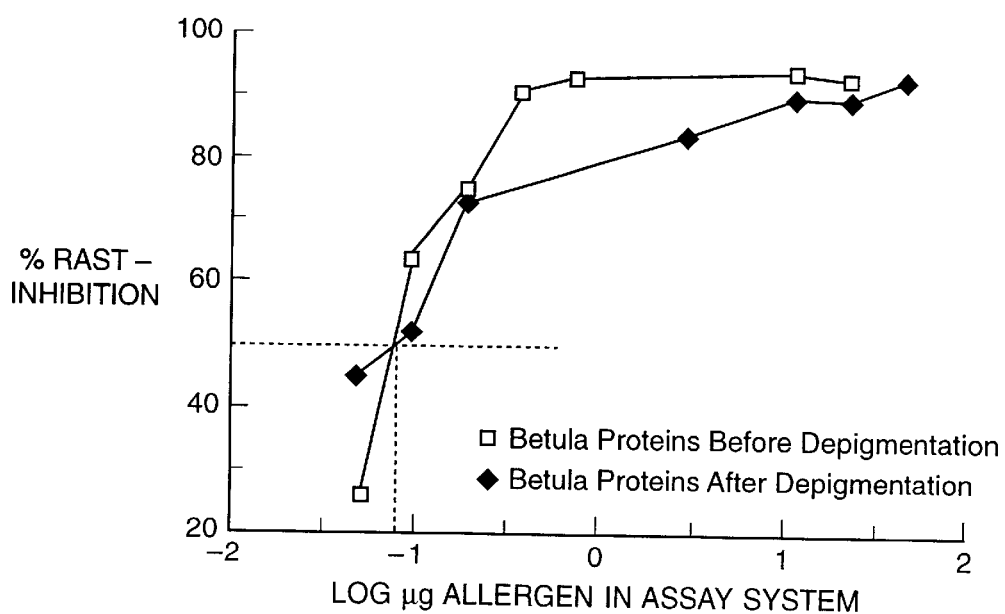
FIG. 3 plots *Betula alba* pollen allergen concentration against IgE-binding potency.

For the inhibition of binding to specific IgE antibodies an established method of RAST-inhibition was chosen. In this method, a serum sample of a patient with pollinosis due to the pollen proteins to be investigated is incubated with a cellulose disc to which either the pollen proteins HMW or the depigmented counterparts DPP have been covalently bound with the aid of cyanogen bromide or another suitable chemical coupling agent. After the capture of specific IgE-antibodies during this incubation phase, the discs are washed in a dilute buffer solution, followed by an incubation step with an enzyme-labelled anti-IgE-antibody, and the colour is finally developed with an enzyme-specific chromogenic substrate. For the evaluation of the IgE-binding potency of a given allergenic protein, sequential dilutions of the allergen are preincubated with a fixed volume of the human serum sample before the capture of residual IgE by the allergen-coated cellulose disc. The IgE-binding potency of the allergenic preparation is read as the point of 50% inhibition from a plot of allergen concentration versus IgE-binding, as shown for the example of *Betula alba* pollen in FIG. 3. In the present Example use was made of two kinds of allergen-coated cellulose discs, viz. discs coupled chemically to the original protein preparation HMW (pigm discs in Table III) and discs coupled chemically to the protein preparations DPP prepared according to Procedure A (depigm discs in Table III). As shown by the collected data in Table III, the allergenic IgE-binding potency of the DPP-proteins tends to decrease slightly, though not significantly, per $\mu$g of lyophilized material in the case of *Betula alba* and *Parietaria judaica*, whereas in the case of the *Olea europea* sample it must be concluded that some loss of IgE-binding epitopes indeed occurs during depigmentation.

It was checked in a separate experiment whether perhaps keeping the Olea HMW proteins at pH 2 by itself had a denaturing effect on the *Olea europea* pollen proteins. To this end, Olea HMW was brought to pH 2 with HCl according to procedure A and the solution was left standing for 4 hours at room temperature. The solution was then readjusted to pH 7.0 without any further dialysis. The preparation was lyophilized and checked for IgE-binding potency by RAST-inhibition, using Olea DPP discs. The results under these conditions of assay and with the particular human serum chosen were: 50% RAST-inhibition for Olea HMW 0.75 $\mu$g, Olea HMW treated at pH 2 and readjusted to pH 7 without dialysis: 0.75 $\mu$g, Olea DPP prepared according to procedure A: 3.89 $\mu$g. Hence, the decrease of IgE-binding allergenicity of Olea pollen DPP relative to Olea HMW is not due to protein denaturation at acid pH, but to removable pigments or other electrostatically adsorbed low-molecular weight organic compounds acting as true antigenic determinants. Comparative studies along these lines underline the usefulness of depigmented pollen proteins for in-depth studies of the molecular structure of antibody-binding allergenic epitopes.

For the inhibition of binding to specific IgG antibodies an established method of enzyme immunoassay was chosen. In this method, a serum sample of a patient with pollinosis due to the pollen proteins to be investigated is incubated with sequential dilutions of the HMW or DPP allergen. The allergen-serum mixtures are then pipetted into the wells of polystyrene microtiter plates pre-coated with either the HMW or DPP proteins by physical adsorption. After 30 minutes at room temperature, the wells are then washed with dilute buffer solution and the specific IgG antibody captured on the allergen-coated plate is determined by treatment with an enzyme-labelled anti IgG-antiserum, followed by colour development with an enzyme-specific chromogenic substrate. The IgG-binding potency of the allergen preparation is evaluated as the point of 50% inhibition interpolated on the plot of allergen concentration versus IgG-binding. In the experiments of this Example III, the microtiter wells were in all cases coated with the DPP-preparations produced according to procedure A. The data in Table III show that the potency of the DPP in IgG-binding increases slightly relative to the HMW products.

TABLE III

Potency of DPP pollen proteins relative to traditional non-depigmented pollen proteins HMW for binding of specific IgE- (by RAST) and IgG-antibodies (by EIA). Figures given represent μg of preparation required for 50% of antibody binding in the test system chosen.

| | Allergen RAST | | | | | |
|---|---|---|---|---|---|---|
| | Pigm discs | | Depigm discs | | EIA for IgG (DPP-coating) | |
| | HMW | DPP | HMW | DPP | HMW | DPP |
| Betula | 0.108 | 0.071 | 0.24 | 0.12 | 46.0 | 17.2 |
| Olea | 0.163 | 1.31 | 0.75 | 4.02 | 0.12 | 0.05 |
| Parietaria | 0.18 | 0.31 | 2.3 | 1.77 | 0.11 | 0.001 |

EXAMPLE IV

In these experiments the original pollen proteins HMW of ragweed (*Ambrosia elatior*) isolated and dialysed at neutral pH were depigmented by free electrophoresis according to procedure C. A solution of 20 mg HMW/ml was made and 5 ml of this solution was brought into a cellophane dialysis bag (Visking dialysis tubing, nominal cut-off 10000 D). The bag was sealed both ends and brought into the rotating plastic holder of the electrophoresis equipment RotaPhor® (BioRad, USA). The void volume of the holder tube was filled with a phosphate buffered-saline solution (0.01M, pH 7.4) and the equipment was put into a cold room at 4° C. Electrophoresis was then started by applying a DC electric potential at a constant power of 12 Watts under continuous rotation of the tube holding the dialysis bag and the outer liquid. The current drupped from 120 mA at the start of the experiment to 68 mA after 3 hours. During the electrophoretic run, the pigments are released from the pollen proteins and migrate out of the dialysis bag to the cathodic compartment of the outer liquid (negative pole). After the run, the depigmented proteins were recovered from the solution inside the dialysis bag and dried by lyophilization. The recovery of DPP product from 100 mg of *Ambrosia elatior* HMW was 69 mg, representing a 69% yield of depigmented material by electrophoresis at neutral pH according to procedure C, as compared to 67% according to procedure A (Table I).

I claim:

1. A process for obtaining aqueous extracts containing allergenically active proteins which are substantially free of adherence to undesirable compounds comprising the steps of a) preparing an aqueous extract containing allergenically active proteins to which undesirable non-allergenic compounds are adhered by electrostatic, hydrophobic or other physical forces;

b) disrupting the electrostatic, hydrophobic or other physical forces under such conditions as to disadhere said non-allergenic compounds from said allergenically active proteins; and c) collecting the resulting aqueous extract, containing allergenically active proteins which are substantially free from adherence to non-allergenic compounds.

2. The process according to claim 1, wherein the non-allergenic compounds have a molecular weight of less than 10,000 daltons.

3. The process according to claim 1, wherein the non-allergenic compounds comprise at least one compound selected from the group consisting of flavonoids and glycosides of flavonoids.

4. The process according to claim 1, wherein the non-allergenic compounds have a molecular weight of less than 5,000 daltons.

5. The process according to claim 1, wherein the electrostatic, hydrophobic or other physical forces are disrupted by at least one chemical selected from the group consisting of acid, alkaline materials including anion- and cation- exchanging materials, salts and electric currents.

6. The process according to claim 5, wherein the acid and alkaline chemicals are used in an amount sufficient to raise an iso-electric point higher than an iso-electric point of said proteins.

7. The process according to claim 5, wherein the electrostatic force is disrupted by an acid having a pH-value of less than 3.

8. The process according to claim 5, wherein the electrostatic force is disrupted by electric currents in the form of electrophoresis.

9. The process according to claim 5, wherein the electrostatic force is disrupted by an acid having a pH-value of 1.5–2.5.

* * * * *